(12) United States Patent
Takaya et al.

(10) Patent No.: US 11,054,240 B2
(45) Date of Patent: Jul. 6, 2021

(54) LIGHT INTERFERENCE UNIT AND LIGHT INTERFERENCE MEASUREMENT DEVICE

(71) Applicants: TATSUTA ELECTRIC WIRE & CABLE CO., LTD., Higashiosaka (JP); NIDEK CO., LTD., Gamagori (JP)

(72) Inventors: Masato Takaya, Kizugawa (JP); Shinya Iwata, Gamagori (JP)

(73) Assignees: TATSUTA ELECTRIC WIRE & CABLE CO., LTD., Higashiosaka (JP); NIDEK CO., LTD., Gamagori (JP)

( * ) Notice: Subject to any disclaimer, the term of this patent is extended or adjusted under 35 U.S.C. 154(b) by 0 days.

(21) Appl. No.: 16/706,995

(22) Filed: Dec. 9, 2019

(65) Prior Publication Data
US 2020/0116471 A1    Apr. 16, 2020

Related U.S. Application Data

(63) Continuation of application No. PCT/JP2018/020464, filed on May 29, 2018.

(30) Foreign Application Priority Data

Jun. 7, 2017    (JP) .............................. JP2017-112500

(51) Int. Cl.
*G01B 9/02*    (2006.01)
*G01B 11/24*   (2006.01)
*A61B 3/10*    (2006.01)

(52) U.S. Cl.
CPC ............ *G01B 9/02* (2013.01); *G01B 9/02015* (2013.01); *G01B 11/24* (2013.01); *A61B 3/10* (2013.01)

(58) Field of Classification Search
CPC .. G01B 9/02; G01B 9/02015; G01B 2290/40; G01B 11/24; G01N 21/17
See application file for complete search history.

(56) References Cited

U.S. PATENT DOCUMENTS

| 9,492,077 | B2 | 11/2016 | Ebersbach et al. |
| 2007/0276269 | A1 | 11/2007 | Yun et al. |

(Continued)

FOREIGN PATENT DOCUMENTS

| EP | 1 925 253 A1 | 5/2008 |
| JP | 2008-128926 A | 6/2008 |

(Continued)

OTHER PUBLICATIONS

Aug. 28, 2018 International Search Report issued in International Patent Application No. PCT/JP2018/020464.

(Continued)

*Primary Examiner* — Jonathan M Hansen
(74) *Attorney, Agent, or Firm* — Oliff PLC

(57) ABSTRACT

A light interference unit includes a branching optical element, a multiplexing optical element, and at least one fiber device. The branching optical element branches a laser light with an emission wavelength temporally swept, into a measurement light and a reference light. The multiplexing optical element multiplexes the reference light and the measurement light reflected by a measured object, and causes them to interfere. The fiber device includes a reference light device. A transmission light path length is a light path length of the reference light transmitting the reference light device, from the reference light device to the multiplexing optical element. A reflection light path length is a light path length of the reference light reflected by a separation portion of the reference light device, from the reference light device to the multiplexing optical element. The transmission light path length is equal to or more than the reflection light path length.

3 Claims, 6 Drawing Sheets

(56) References Cited

U.S. PATENT DOCUMENTS

| | | | |
|---|---|---|---|
| 2008/0123092 A1* | 5/2008 | Hatori | ................ G01N 21/4795 |
| | | | 356/300 |
| 2013/0308097 A1 | 11/2013 | Ebersbach et al. | |
| 2014/0228681 A1 | 8/2014 | Jia et al. | |
| 2016/0367134 A1 | 12/2016 | Su | |
| 2017/0311795 A1* | 11/2017 | Sumiya | ................ G02B 6/0008 |

FOREIGN PATENT DOCUMENTS

| | | |
|---|---|---|
| JP | 2009-536740 A | 10/2009 |
| JP | 2014-226173 A | 12/2014 |
| JP | 2015-511146 A | 4/2015 |
| JP | 2015-198757 A | 11/2015 |
| WO | 2016/115387 A1 | 7/2016 |
| WO | 2019/062484 A1 | 4/2019 |

OTHER PUBLICATIONS

Aug. 28, 2018 Written Opinion of the International Searching Authority issued in International Patent Application No. PCT/JP2018/020464.

Jan. 2, 2020 Publication Submission Form issued in Japanese Patent Application No. 2017-112500.

Jul. 13, 2020 Office Action issued in Japanese Patent Application No. 2017-112500.

Feb. 10, 2021 Extended European Search Report issued in European Patent Application No. 18813050.4.

Jan. 21, 2021 Office Action issued in Chinese Patent Application No. 201880037887.8.

* cited by examiner

LIGHT INTERFERENCE UNIT AND LIGHT INTERFERENCE MEASUREMENT DEVICE

CROSS REFERENCE TO RELATED APPLICATION

This application is a continuation application of International Application No. PCT/JP2018/020464, filed on May 29, 2018, which claims priority from Japanese Patent Application No. 2017-112500, filed on Jun. 7, 2017. The disclosure of the foregoing application is hereby incorporated by reference in its entirety.

BACKGROUND

The present disclosure relates to a light interference unit and a light interference measurement device.

Conventionally, a light interference unit including a branching optical element, a multiplexing optical element and a fiber device has been known. The branching optical element branches light output from a light source. The multiplexing optical element multiplexes the branched lights. The fiber device includes a separation portion. In the separation portion, the light introduced by an optical fiber is temporarily separated from a core of the optical fiber to an outside having a refractive index different from that of the core and then is incident on the core again. The fiber device has at least one of functions of, for example, attenuating the light, adjusting a light path, and the like. For example, a tomographic image reading portion disclosed in Japanese Unexamined Patent Application Publication No. 2014-226173 includes a fiber coupler, which is one example of the branching optical element, a fiber coupler, which is one example of the multiplexing optical element, and a delay line unit, which is one example of the fiber device. The delay line unit adjusts a light path length of a reference light. The reference light is one light branched by the fiber coupler. Another fiber coupler multiplexes the reference light, for which the light path length is adjusted, with a measurement light. The measurement light is another light branched by the fiber coupler. The reference light and the measurement light are multiplexed, so that interference light is generated. An interference signal of the interference light is measured by a detector for each wavelength.

SUMMARY

In the fiber device, when the light is separated from the core of the optical fiber to the outside and when the light is incident on the core again in the fiber device, the light is reflected in the separation portion. The inventors of the present application found that a noise is generated in a whole waveform of the interference signal due to an influence of the fiber device in a case in which a laser light for which an emission wavelength is temporally swept is used. The cause of the noise generated in the whole waveform has not been precisely realized, however it is assumed that the noise is generated due to a reflection light reflected by the separation portion of the fiber device.

Embodiments of the broad principles derived herein provide a light interference unit and a light interference measurement device that reduce a noise generated in a whole waveform of an interference signal.

Embodiments provide a light interference unit that includes a branching optical element, a multiplexing optical element, and at least one fiber device. The branching optical element branches a laser light for which an emission wavelength is temporally swept, into a measurement light and a reference light. The multiplexing optical element multiplexes the reference light and the measurement light reflected by an object to be measured, and causes the reference light and the measurement light to interfere. The at least one fiber device is provided with a separation portion in which the laser light introduced by an optical fiber is temporarily separated from a core of the optical fiber to an outside having a refractive index different from that of the core and then is incident on the core again. The at least one fiber device includes a reference light device served as the fiber device arranged on a light path for the reference light between the branching optical element and the multiplexing optical element. As a transmission light path length is defined by a light path length of the reference light, which transmits the reference light device, from the reference light device to the multiplexing optical element, and a reflection light path length is defined by a light path length of the reference light, which is reflected by the separation portion of the reference light device, from the reference light device to the multiplexing optical element, the transmission light path length is equal to or more than the reflection light path length.

Embodiments further provide a light interference measurement device that includes a wavelength sweeping light source, a branching optical element, a multiplexing optical element, at least one fiber device, and a detector. The wavelength sweeping light source emits a laser light for which an emission wavelength is temporally swept. The branching optical element branches the laser light emitted from the wavelength sweeping light source, into a measurement light and a reference light. The multiplexing optical element multiplexes the reference light and the measurement light reflected by an object to be measured, and causes the reference light and the measurement light to interfere. The at least one fiber device is provided with a separation portion in which the laser light introduced by an optical fiber is temporarily separated from a core of the optical fiber to an outside having a refractive index different from that of the core and then is incident on the core again. The detector detects an interference signal of an interference light generated by the multiplexing optical element. The at least one fiber device includes a reference light device served as the fiber device arranged on a light path for the reference light between the branching optical element and the multiplexing optical element. As a transmission light path length is defined by a light path length of the laser light, which transmits the reference light device, from the reference light device to the multiplexing optical element, and a reflection light path length is defined by a light path length of the laser light, which is reflected by the reference light device, from the reference light device to the multiplexing optical element, the transmission light path length is equal to or more than the reflection light path length.

According to each of the light interference unit and the light interference measurement device in the present disclosure, a noise generated in a whole waveform of the interference signal is appropriately decreased.

DETAILED DESCRIPTION

Figure 1:
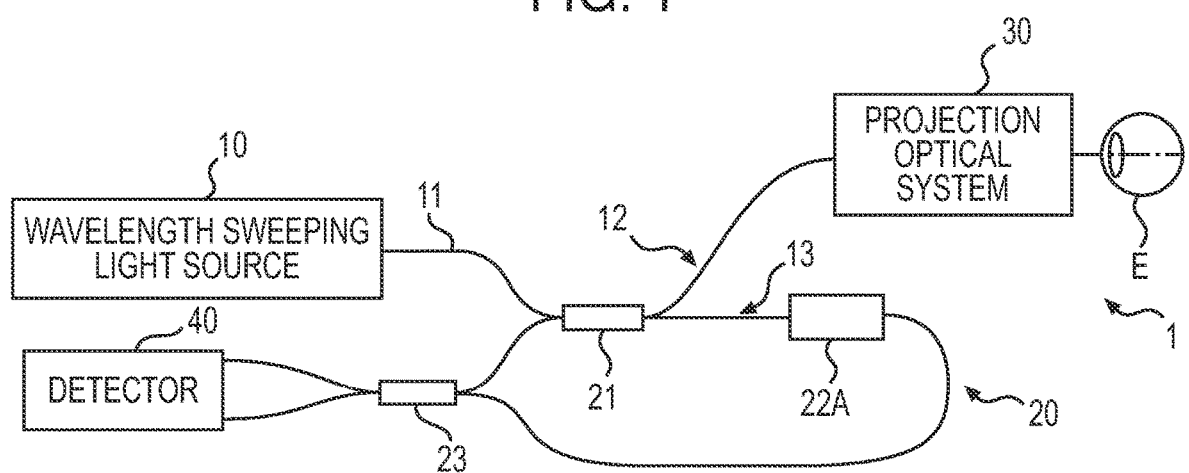
FIG. 1 is a schematic view illustrating a configuration of a light interference measurement device 1 according to a first embodiment.

A first aspect of the light interference unit exemplarily described in the present disclosure includes a branching optical element, a multiplexing optical element, and at least one fiber device. The branching optical element branches a laser light for which an emission wavelength is temporally swept, into a measurement light and a reference light. The multiplexing optical element multiplexes the reference light and the measurement light reflected by an object to be measured, and causes the reference light and the measurement light to interfere. The at least one fiber device is provided with a separation portion in which the laser light introduced by an optical fiber is temporarily separated from a core of the optical fiber to an outside having a refractive index different from that of the core and then is incident on the core again. The at least one fiber device includes a reference light device served as the fiber device arranged on a light path for the reference light between the branching optical element and the multiplexing optical element. As a transmission light path length is defined by a light path length of the reference light, which transmits the reference light device, from the reference light device to the multiplexing optical element, and a reflection light path length is defined by a light path length of the reference light, which is reflected by the separation portion of the reference light device, from the reference light device to the multiplexing optical element, the transmission light path length is equal to or more than the reflection light path length. That is, the reference light device is arranged such that the transmission light path length is equal to or more than the reflection light path length. In this case, a noise generated in a whole waveform of an interference signal due to the reference light device is appropriately decreased. Consequently, the object to be measured can be measured further precisely based on the detected interference signal. Further, the necessity for removing the noise through a data processing after the detection is decreased, and thereby the processing time can be shortened.

The number of the reference light devices may be one or more. In a case in which a plurality of the reference light devices is provided, it is preferable that each of the reference light devices fulfills an arrangement relation in which the transmission light path length is equal to or more than the reflection light path length. However, at least the reference light device closest to the branching optical element on the light path for the reference light between the branching optical element and the multiplexing optical element may fulfill the arrangement relation. The reference light device closest to the branching optical element corresponds to the reference light device arranged at the most upstream side on the light path for the reference light.

A second aspect of the light interference unit exemplarily described in the present disclosure includes a branching optical element, a multiplexing optical element, and at least one fiber device. The branching optical element branches a laser light for which an emission wavelength is temporally swept, into a measurement light and a reference light. The multiplexing optical element multiplexes the reference light and the measurement light reflected by an object to be measured, and causes the reference light and the measurement light to interfere. The at least one fiber device includes a separation portion. In the separation portion, the laser light introduced by an optical fiber is temporarily separated from a core of the optical fiber to an outside having a refractive index different from that of the core and then is incident on the core again. The at least one fiber device includes a measurement light device. The measurement light device is served as the fiber device arranged on a light path for the measurement light between the branching optical element and the object to be measured. As a transmission light path length is defined by a light path length of the reference light from the branching optical element to the multiplexing optical element, and a reflection light path length is defined by a light path length of the measurement light from the branching optical element to the multiplexing optical element passing the branching optical element again after the measurement light is reflected by the measurement light device, the transmission light path length is equal to or more than the reflection light path length. That is, the measurement light device is arranged such that the transmission light path length is equal to or more than the reflection light path length. In this case, a noise generated in a whole waveform of an interference signal due to the measurement light device is appropriately decreased. Consequently, the object to be measured can be measured further precisely based on the detected interference signal. Further, the necessity for removing the noise through a data processing after the detection is decreased, and thereby the processing time can be shortened.

The number of the measurement light devices may be one or more. In a case in which a plurality of the measurement light devices is provided, it is preferable that each of the measurement light devices fulfills an arrangement relation in which the transmission light path length is equal to or more than the reflection light path length. However, at least the measurement light device closest to the branching optical element on the light path for the measurement light between the branching optical element and the object to be measured may fulfill the arrangement relation. The measurement light device closest to the branching optical element corresponds to the measurement light device arranged at the most upstream side on the light path for the measurement light.

The fiber device may be formed by an attenuator (attenuator), an optical delay portion (optical delay line), a circulator, or an isolator. The attenuator adjusts output of the laser light. The optical delay portion adjusts a light path length of the laser light. In the attenuator, the optical delay portion, the circulator, or the isolator, each of which having a separation portion, a part of the laser light is reflected by the separation portion. Against this, with a configuration that fulfills the arrangement relation in which the transmission light path length is equal to or more than the reflection light path length, an influence of a noise due to a reflection light caused by the separation portion is decreased and the light path is adjusted further precisely.

Various devices having the separation portion may be adopted as the fiber device. In the separation portion, the laser light introduced by the optical fiber is temporarily separated from the core of the optical fiber to the outside having the refractive index different from that of the core and then is incident on the core again. Examples of the fiber device include a filter type coupler and a fiber connector.

A first aspect of the light interference measurement device exemplarily described in the present disclosure includes a wavelength sweeping light source, a branching optical element, a multiplexing optical element, at least one fiber device, and a detector. The wavelength sweeping light source emits a laser light for which an emission wavelength is temporally swept. The branching optical element branches the laser light emitted from the wavelength sweeping light source, into a measurement light and a reference light. The multiplexing optical element multiplexes the reference light and the measurement light reflected by an object to be measured, and causes the reference light and the measurement light to interfere. The at least one fiber device includes a separation portion. The detector detects an interference signal of an interference light generated by the multiplexing optical element. In the separation portion, the laser light introduced by an optical fiber is temporarily separated from a core of the optical fiber to an outside having a refractive index different from that of the core and then is incident on the core again. The at least one fiber device includes a reference light device. The reference light device is served as the fiber device arranged on a light path for the reference light between the branching optical element and the multiplexing optical element. As a transmission light path length is defined by a light path length of the laser light, which transmits the reference light device, from the reference light device to the multiplexing optical element, and a reflection light path length is defined by a light path length of the laser light, which is reflected by the reference light device, from the reference light device to the multiplexing optical element, the transmission light path length is equal to or more than the reflection light path length. That is, the reference light device is arranged such that the transmission light path length is equal to or more than the reflection light path length. In this case, a noise generated in a whole waveform of an interference signal due to the reference light device is appropriately decreased. Consequently, the object to be measured can be measured further precisely based on the detected interference signal. Further, the necessity for removing the noise through a data processing after the detection is decreased, and thereby the processing time can be shortened.

A second aspect of the light interference measurement device exemplarily described in the present disclosure includes a wavelength sweeping light source, a branching optical element, a multiplexing optical element, at least one fiber device, and a detector. The wavelength sweeping light source emits a laser light for which an emission wavelength is temporally swept. The branching optical element branches the laser light emitted from the wavelength sweeping light source, into a measurement light and a reference light. The multiplexing optical element multiplexes the reference light and the measurement light reflected by an object to be measured, and causes the reference light and the measurement light to interfere. The at least one fiber device includes a separation portion. In the separation portion, the laser light introduced by an optical fiber is temporarily separated from a core of the optical fiber to an outside having a refractive index different from that of the core and then is incident on the core again. The detector detects an interference signal of an interference light generated by the multiplexing optical element. The at least one fiber device includes a measurement light device. The measurement light device is served as the fiber device arranged on a light path for the measurement light between the branching optical element and the object to be measured. As a transmission light path length is defined by a light path length of the reference light from the branching optical element to the multiplexing optical element, and a reflection light path length is defined by a light path length of the measurement light from the branching optical element to the multiplexing optical element passing the branching optical element again after the measurement light is reflected by the measurement light device, the transmission light path length is equal to or more than the reflection light path length. That is, the measurement light device is arranged such that the transmission light path length is equal to or more than the reflection light path length. In this case, a noise generated in a whole waveform of an interference signal due to the measurement light device is appropriately decreased. Consequently, the object to be measured can be measured further precisely based on the detected interference signal. Further, the necessity for removing the noise through a data processing after the detection is decreased, and thereby the processing time can be shortened.

Hereinafter, exemplary embodiments of the present disclosure will be described with reference to the drawings. At first, a schematic configuration of a light interference measurement device 1 according to a first embodiment is described with reference to FIG. 1 and FIG. 2. The light interference measurement device 1 is a light coherence tomography device. As shown in FIG. 1, the light interference measurement device 1 is provided with a wavelength sweeping light source 10, a light interference unit 20, a projection optical system 30, and a detector 40.

The wavelength sweeping light source 10 emits a laser light for acquiring internal information of an object to be measured (eye E in the present embodiment), into an optical fiber 11. The wavelength sweeping light source 10 is formed as a wavelength scanning type light source that temporally changes an emission wavelength at a high speed. For example, the wavelength sweeping light source 10 may include a laser medium, a resonator, and a wavelength selecting filter. The wavelength selecting filter may be formed by, for example, a combination of a diffraction grating and a polygon mirror, or a filter using a Fabry-Perot etalon.

The light interference unit 20 includes a branching optical element 21, at least one fiber device 22, and a multiplexing optical element 23. The branching optical element 21 branches the laser light emitted from the wavelength sweeping light source 10 into a measurement light and a reference light and introduces them to a measurement light path 12 and a reference light path 13, respectively. As one example, the branching optical element 21 of the present embodiment is formed by a fiber coupler. However, other element other than the fiber coupler (for example, a circulator, a beam splitter, or the like) may be adopted as the branching optical element 21.

The at least one fiber device 22 includes a fiber device 22 (hereinafter, also referred to as "reference light device 22A") arranged on the reference light path 13 between the branching optical element 21 and the multiplexing optical element 23. The light interference measurement device 1 and the light interference unit 20 may include, for example, one reference light device 22A as the at least one fiber device 22. The light interference measurement device 1 and the light interference unit 20 may include the fiber device 22 on a light path other than the reference light path 13. Further, the light interference measurement device 1 and the light interference unit 20 may include a plurality of the fiber devices 22 on the reference light path 13.

Figure 2:
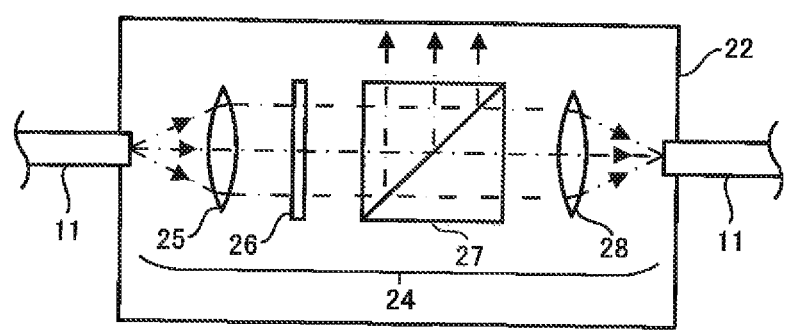
FIG. 2 is a schematic view illustrating a configuration of a fiber device 22.

The fiber device 22 has at least one of functions of, for example, attenuating the laser light, adjusting the light path, and the like. As one example, the fiber device 22 of the present embodiment is formed by an attenuator (attenuator) that adjusts output of the laser light. As shown in FIG. 2, the fiber device 22 includes a separation portion 24. In the separation portion 24, the laser light introduced by the optical fiber 11 is temporarily separated from a core of the optical fiber 11 to an outside having a refractive index different from that of the core and then is incident on the core again. In the example shown in FIG. 2, the outside is in the air. For example, the air has a refractive index different from that of the core. In the example shown in FIG. 2, the separation portion 24 includes a collimator lens 25, a wavelength plate 26, a beam splitter 27, and a condensing lens 28.

In the separation portion 24, the laser light separated from the optical fiber 11 is turned into a parallel light after passing the collimator lens 25. When the laser light passing the collimator lens 25 passes the wavelength plate 26, a phase difference (light path difference) is generated in a polarization component orthogonal to the laser light. After that, the laser light is branched by the beam splitter 27 into a laser light that transmits the beam splitter 27 and a laser light reflected by the beam splitter 27. The laser light that transmits the beam splitter 27 is incident on the core of the optical fiber 11 again. A transmission rate of the laser light transmitting the beam splitter 27 is adjusted by revolving the wavelength plate 26.

The multiplexing optical element 23 multiplexes the reference light and the measurement light reflected by the object to be measured, and causes them to interfere. In the first embodiment, the reference light multiplexed with the measurement light by the multiplexing optical element 23 is a laser light that transmits the optical fiber 11 and the reference light device 22A on the reference light path 13. That is, in the first embodiment, a reference optical system that generates the reference light is formed as a transmission optical system that does not return the light into the branching optical element 21 but transmits the light through the multiplexing optical element 23 so as to generate the reference light. The measurement light multiplexed with the reference light by the multiplexing optical element 23 is a laser light that transmits the optical fiber 11 and the projection optical system 30 on the measurement light path 12, and transmits the projection optical system 30 and the branching optical element 21 after being reflected by the object to be measured. As one example, the multiplexing optical element 23 of the present embodiment is formed by a fiber coupler. However, other element other than the fiber coupler may be adopted as the multiplexing optical element 23.

The projection optical system 30 introduces the measurement light into the object to be measured, and introduces the reflection light of the measurement light reflected by the object to be measured into the optical fiber 11 of the measurement light path 12. The object to be measured is, for example, a fundus, an anterior ocular segment, or the like of the eye E. The projection optical system 30 of the present embodiment includes an optical scanner and an objective lens system. The measurement light is introduced to the optical scanner through the optical fiber 11. The optical scanner deflects a deflection direction of the measurement light. The measurement light deflected by the optical scanner is turned into a parallel beam by the objective lens system and is incident on the object to be measured. The optical scanner causes the measurement light to scan in a XY direction (crossing direction) in the object to be measured. Various components capable of deflecting a forward direction of the light may be adopted as the optical scanner. Examples of the various components capable of deflecting the forward direction of the light include a galvanometer mirror, a polygon mirror, a resonant scanner, an acoustic optical element, and the like. As one example, two galvanometer mirrors are adopted as the optical scanner in the present embodiment.

The detector 40 detects the interference signal of the interference light generated by the multiplexing optical element 23. The light interference measurement device 1 measures the object to be measured based on the interference signal detected by the detector 40.

When the laser light introduced by the optical fiber 11 is temporally separated to the outside and is incident on the core again, the light is reflected in the separation portion 24 due to a difference of the refractive indexes between the core and the separation portion 24. The inventors of the present application found that a noise is generated in a whole waveform of the interference signal due to an influence of the reference light device 22A in a case in which the laser light for which an emission wavelength is temporally swept is used. The noise is assumed to be generated due to the reflection light reflected by the separation portion 24 of the reference light device 22A. In the first embodiment, a transmission light path length is defined by a light path length of the reference light, which transmits the reference light device 22A, from the reference light device 22A to the multiplexing optical element 23. A reflection light path length is defined by a light path length of the reference light, which is reflected by the separation portion 24 of the reference light device 22A, from the reference light device 22A to the multiplexing optical element 23 through the branching optical element 21. In the first embodiment, respective elements are arranged such that the transmission light path length is equal to or more than the reflection light path length. That is, the reference light device 22A is arranged such that the transmission light path length is equal to or more than the reflection light path length. In this case, the inventors of the present application found through an experiment that the noise generated in the whole waveform of the interference signal is appropriately decreased (details are described below). Consequently, according to the light interference measurement device 1 and the light interference unit 20 of the first embodiment, even in a case in which the reference light device 22A is arranged on the reference light path 13, the object to be measured can be measured further precisely based on the detected interference signal. Further, the necessity for removing the noise through a data processing after the detection is decreased, and thereby the processing time can be shortened.

It is preferable that the reference light device 22A is arranged such that the transmission light path length is equal to three second or more of the reflection light path length. It is more preferable that the reference light device 22A is arranged such that the transmission light path length is equal to seven third or more of the reflection light path length. In this case, the noise generated in the whole waveform of the interference signal is further appropriately decreased.

The number of the reference light devices 22A may be one or more. In a case in which a plurality of the reference light devices 22A is provided, it is preferable that each of the reference light devices 22A fulfills the arrangement relation described above (for example, the arrangement relation in which the transmission light path length is equal to or more than the reflection light path length). However, at least the reference light device 22A closest to the branching optical element 21 on the reference light path 13 between the branching optical element 21 and the multiplexing optical element 23 may fulfill the arrangement relation. The reference light device closest to the branching optical element 21 corresponds to the reference light device 22A arranged at the most upstream side on the reference light path 13.

Figure 3:
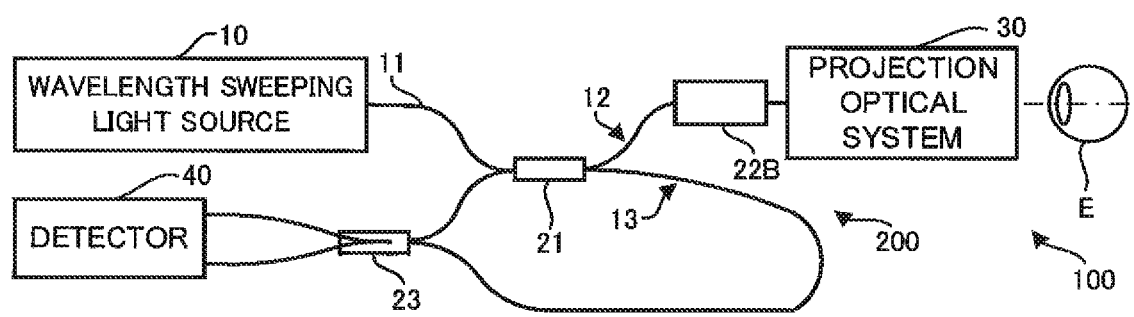
FIG. 3 is a schematic view illustrating a configuration of a light interference measurement device 100 according to a second embodiment.

Next, a schematic configuration of a light interference measurement device 100 according to a second embodiment is described with reference to FIG. 2 and FIG. 3. Hereinafter, the same sign is assigned to the same configuration, and the description thereof is omitted or simplified. Therefore, the configuration different from that of the first embodiment is described. The light interference measurement device 100 according to the second embodiment is a light coherent tomography device. As shown in FIG. 3, the light interference measurement device 100 is provided with a wavelength sweeping light source 10, a light interference unit 200, a projection optical system 30, and a detector 40.

The light interference unit 200 includes a branching optical element 21, at least one fiber device 22, and a multiplexing optical element 23. The at least one fiber device 22 includes a fiber device 22 (hereinafter, also referred to as "measurement light device 22B") arranged on a measurement light path 12 between the branching optical element 21 and an object to be measured. The same configuration as the fiber device 22 exemplarily shown in FIG. 2 can be adopted in the measurement light device 22B of the second embodiment, and therefore a detailed description of the measurement light device 22B is omitted. The light interference measurement device 100 and the light interference unit 200 may include, for example, one measurement light device 22B as the at least one fiber device 22. The light interference measurement device 100 and the light interference unit 200 may include the fiber device 22 on a light path other than the measurement light path 12. Further, the light interference measurement device 100 and the light interference unit 200 may include a plurality of the fiber devices 22 on the measurement light path 12.

The multiplexing optical element 23 multiplexes the reference light and the measurement light reflected by the object to be measured, and causes them to interfere. In the second embodiment, the reference light multiplexed with the measurement light by the multiplexing optical element 23 is a laser light that transmits the optical fiber 11 on the reference light path 13. That is, in the second embodiment, similar to the first embodiment, the reference optical system that generates the reference light is formed as a transmission optical system. The measurement light multiplexed with the reference light by the multiplexing optical element 23 is a laser light that transmits the optical fiber 11, the measurement light device 22B and the projection optical system 30 on the measurement light path 12, and transmits the projection optical system 30, the measurement light device 22B and the branching optical element 21 after being reflected by the object to be measured.

In the second embodiment, a transmission light path length is defined by a light path length of the reference light from the branching optical element 21 to the multiplexing optical element 23. A reflection light path length is defined by a light path length of the measurement light from the branching optical element 21 to the multiplexing optical element 23 passing the branching optical element 21 again after the measurement light is reflected by the measurement light device 22B. In the second embodiment, respective elements are arranged such that the transmission light path length is equal to or more than the reflection light path length. That is, the measurement light device 22B is arranged such that the transmission light path length is equal to or more than the reflection light path length. Also in this case, the noise generated in the whole waveform of the interference signal due to the measurement light device 22B is appropriately decreased. Consequently, the object to be measured can be measured further precisely based on the detected interference signal. Further, the necessity for removing the noise through a data processing after the detection is decreased, and thereby the processing time can be shortened.

In the second embodiment, it is preferable that the measurement light device 22B is arranged such that the transmission light path length is equal to three second or more of the reflection light path length. It is more preferable that the measurement light device 22B is arranged such that the transmission light path length is equal to seven third or more of the reflection light path length. In this case, the noise generated in the whole waveform of the interference signal is further appropriately decreased.

The number of the measurement light devices 22B may be one or more. In a case in which a plurality of the measurement light devices 22B is provided, it is preferable that each of the measurement light devices 22B fulfills the arrangement relation described above (for example, the arrangement relation in which the transmission light path length is equal to or more than the reflection light path length). However, at least the measurement light device 22B closest to the branching optical element 21 on the measurement light path 12 between the branching optical element 21 and the object to be measured may fulfill the arrangement relation. The measurement light device closest to the branching optical element 21 corresponds to the measurement light device 22B arranged at the most upstream side on the measurement light path 12.

Various modifications can be applied to each of the embodiments described above. In the embodiment described above, each of the light interference measurement device 1 and the light interference unit 100 is formed as a light coherence tomography device. However, each of the light interference measurement device 1 and the light interference unit 100 may be formed as a light interference measurement device other than the light coherence tomography device (for example, an ocular axial length measurement device that measures an ocular axial length). In this case, each configuration (for example, a configuration of the projection optical system 30 or the like) may be designed appropriately in accordance with a type of the device.

Various devices having a separation portion in which a laser light introduced by an optical fiber is temporally separated from a core of the optical fiber to an outside having a refractive index different from that of the core and then is incident on the core again may be adopted as the fiber device 22.

In the examples of the embodiments described above, the fiber device 22 is formed by an attenuator that adjusts the output of the laser light. However, the fiber device 22 may be formed by a device other than an attenuator. For example, the fiber device 22 may be formed by an optical delay portion (optical delay line) that adjusts a light path length for the laser light. In the optical delay portion having the separation portion, a part of the laser light is reflected by the separation portion, similar to the attenuator. Against this, with a configuration in which each of the reference light device 22A and the measurement light device 22B fulfills the arrangement relation in which the transmission light path length is equal to or more than the reflection light path length, an influence of a noise due to the reflection light caused by the separation portion is decreased and the light path is adjusted further precisely.

The fiber device 22 may be formed by a circulator or an isolator. A combination of a circulator and a mirror may be used as an optical delay device. Further, the fiber device 22 may be formed by a filter type coupler having a collimator and a filter. The filter type coupler branches a laser light and multiplexes the laser lights using a characteristic of the filter. Further, the fiber device 22 may be formed by a fiber connector. Each of the circulator, the isolator, the fiber type coupler, and the fiber connector also has the separation portion. With a configuration in which each of the reference light device 22A and the measurement light device 22B fulfills the arrangement relation in which the transmission light path length is equal to or more than the reflection light path length, an influence of a noise due to the reflection light caused by the separation portion is decreased and the light path is adjusted.

The fiber device 22 may not be formed by an optical variable attenuator in which an attenuation amount of the laser light is variable as described in the embodiments described above but formed by an optical fixed attenuator in which the attenuation amount of the laser light is fixed.

Measurement results of a noise generated in the interference signal of an example, a first comparative example, and a second comparative example are described with reference to FIG. 4 through FIG. 6. In the example, the first comparative example, and the second comparative example, a light interference unit and a light interference measurement device are similar to the light interference unit 20 and the light interference measurement device 1 according to the first embodiment, however positions of the reference light devices 22A are different from each other. In the example (see FIG. 4), "transmission light path length:reflection light path length=1.3:1" is fulfilled. That is, in the example, the reference light device 22A is arranged such that the transmission light path length is more than the reflection light path length. In the first comparative example (see FIG. 5), "transmission light path length:reflection light path length=1:1" is fulfilled. That is, in the first comparative example, the reference light device 22A is arranged such that the transmission light path length is substantially equal to the reflection light path length. Accordingly, in each of the example and the first comparative example, the reference light device 22A fulfills the arrangement relation described in the first embodiment. While, in the second comparative example (see FIG. 6), "transmission light path length:reflection light path length=0.6:1" is fulfilled. That is, in the second comparative example, the reference light device 22A is arranged such that the transmission light path length is less than the reflection light path length. Accordingly, in the second comparative example, the reference light device 22A does not fulfill the arrangement relation described in the first embodiment.

Figure 4:
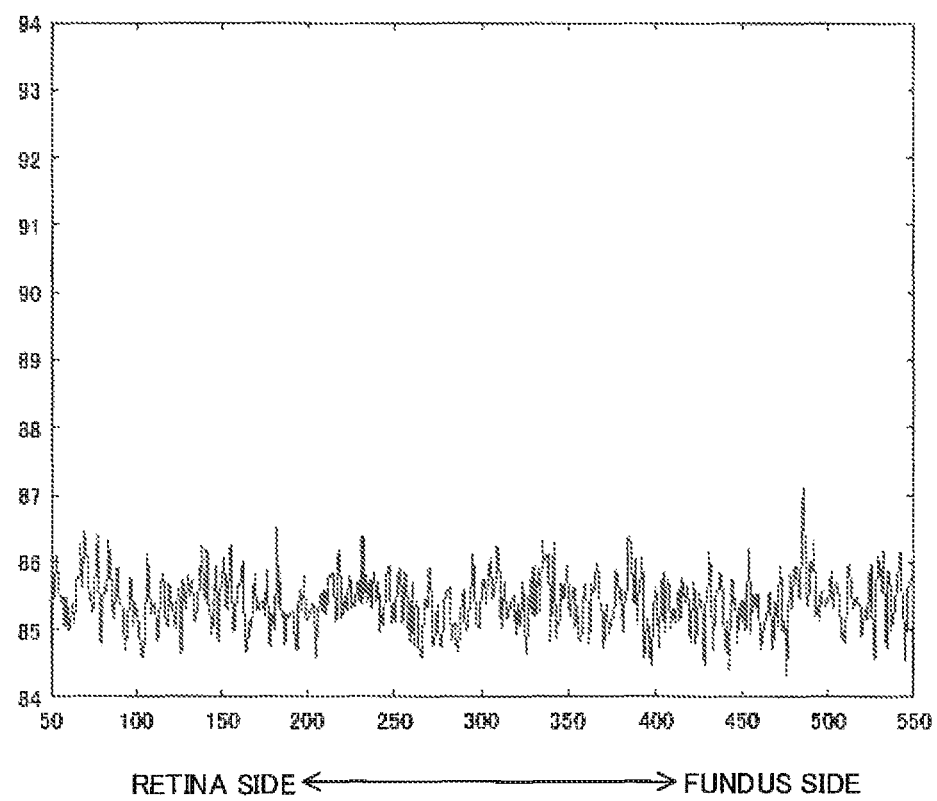
FIG. 4 is a graph illustrating a measurement result of an example.
Figure 5:
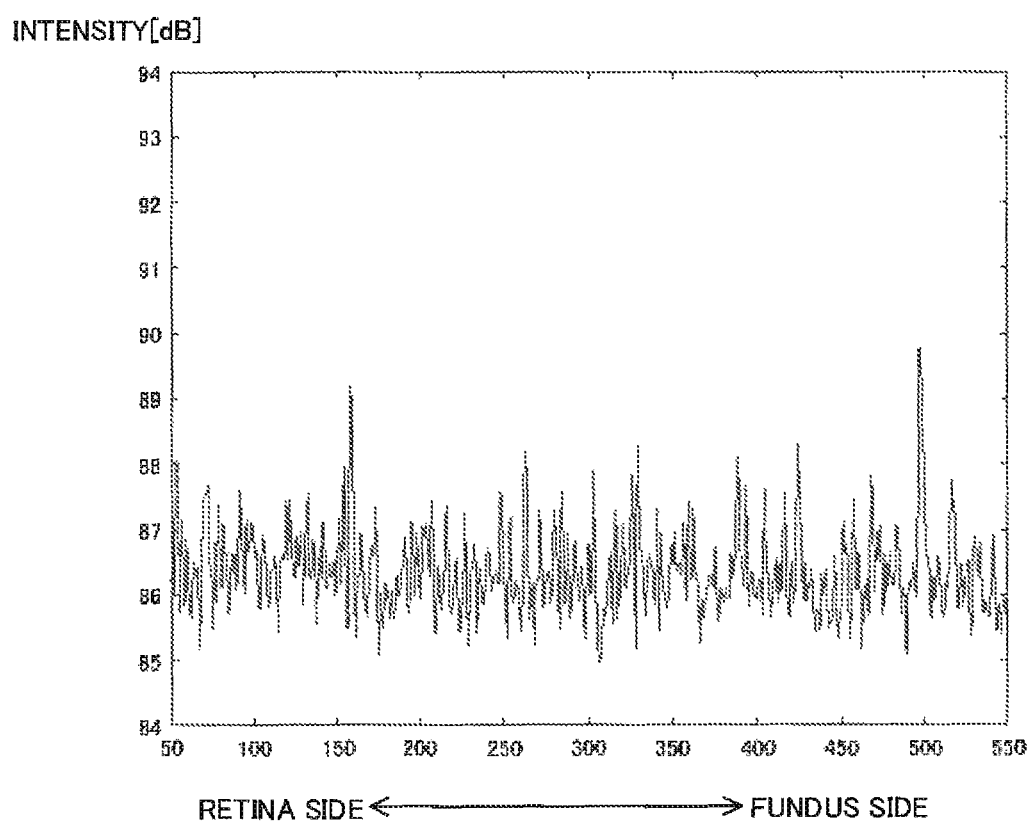
FIG. 5 is a graph illustrating a measurement result of a first comparative example.
Figure 6:
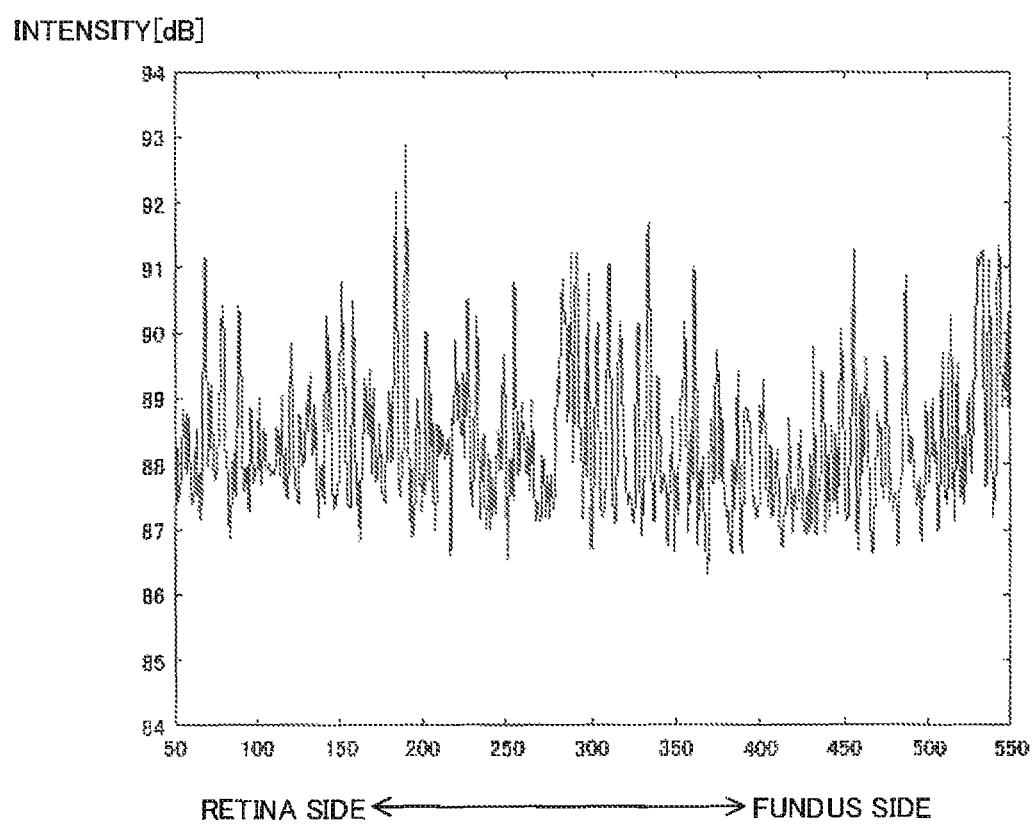
FIG. 6 is a graph illustrating a measurement result of a second comparative example.

In each of FIG. 4 through FIG. 6, a vertical axis of the graph denotes intensity (dB) of the noise. A horizontal axis of the graph denotes a point corresponding to a position in a Z direction of the object to be measured. The Z direction denotes an incident direction of the laser light on the object to be measured. In the experiment, the object to be measured is an eye E. In the horizontal axis, a side having a smaller value is a retina side, and a side having a larger value is a fundus side. As shown in FIG. 4, in the example, the noise is generated in the interference signal in range between 84 dB and 88 dB. As shown in FIG. 5, in the first comparative example, the noise is generated in the interferences signal in a range between 84 dB and 90 dB. As shown in FIG. 6, in the second comparative example, the noise is generated in the interferences signal in a range between 86 dB and 93 dB.

In the example, the intensity of the noise generated in the interference signal is small, compared to the first comparative example and the second comparative example. In the first comparative example, the intensity of the noise generated in the interference signal is small, compared to the second comparative example. In the second comparative example, a large noise is generated in the interference signal, compared to the example and the first comparative example. Based on the measurement result of the present experiment, it is found that, in a case in which the reference light device 22A is arranged such that the transmission light path length is equal to or more than the reflection light path length, the noise generated in the whole waveform of the interference signal is appropriately decreased. Further, it is found that the noise is decreased in a case in which the transmission light path length is more than the reflection light path length more than a case in which the transmission light path length is substantially equal to the reflection light path length.

The apparatus and methods described above with reference to the various embodiments are merely examples. It goes without saying that they are not confined to the depicted embodiments. While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying principles.

What is claimed is:

1. A light interference unit comprising:
   a branching optical element that branches a laser light for which an emission wavelength is temporally swept, into a measurement light and a reference light;
   a multiplexing optical element that multiplexes the reference light and the measurement light reflected by an object to be measured, and causes the reference light and the measurement light to interfere; and
   at least one fiber device provided with a separation portion in which the laser light introduced by an optical fiber is temporarily separated from a core of the optical fiber to an outside having a refractive index different from that of the core and then is incident on the core again,
   wherein the at least one fiber device includes a reference light device which is served as the fiber device with the separation portion and is arranged on a light path for the reference light between the branching optical element and the multiplexing optical element, and
   wherein,
      a transmission light path length is a light path length of the reference light which transmits the reference light device, and the transmission light path length is defined from the reference light device to the multiplexing optical element, and
      a reflection light path length is a light path length of the reference light which is reflected by the separation portion of the reference light device and reaches the multiplexing optical element without passing the reference light device, and the reflection light path length is defined from the reference light device to the multiplexing optical element through the branching optical element, and
      the transmission light path length is equal to or more than the reflection light path length.

2. The light interference unit according to claim 1, wherein the fiber device is formed by an attenuator that adjusts output of the laser light, an optical delay portion that adjusts a light path length of the laser light, a circulator, or an isolator.

3. A light interference measurement device comprising:
- a wavelength sweeping light source that emits a laser light for which an emission wavelength is temporally swept;
- a branching optical element that branches the laser light emitted from the wavelength sweeping light source, into a measurement light and a reference light;
- a multiplexing optical element that multiplexes the reference light and the measurement light reflected by an object to be measured, and causes the reference light and the measurement light to interfere;
- at least one fiber device provided with a separation portion in which the laser light introduced by an optical fiber is temporarily separated from a core of the optical fiber to an outside having a refractive index different from that of the core and then is incident on the core again; and
- a detector that detects an interference signal of an interference light generated by the multiplexing optical element, wherein the at least one fiber device includes a reference light device which is served as the fiber device with the separation portion and is arranged on a light path for the reference light between the branching optical element and the multiplexing optical element, and wherein,
- a transmission light path length is a light path length of the laser light which transmits the reference light device, and the transmission light path length is defined from the reference light device to the multiplexing optical element, and
- a reflection light path length is a light path length of the laser light which is reflected by the reference light device and reaches the multiplexing optical element without passing the reference light device, and the reflection light path length is defined from the reference light device to the multiplexing optical element through the branching optical element, and
- the transmission light path length is equal to or more than the reflection light path length.

* * * * *